U S010234268B2

(12) United States Patent
Cheng et al.

(10) Patent No.: US 10,234,268 B2
(45) Date of Patent: Mar. 19, 2019

(54) METHOD AND APPARATUS FOR DIGITAL HOLOGRAPHIC MICROTOMOGRAPHY

(71) Applicant: National Taiwan Normal University, Taipei (TW)

(72) Inventors: Chau-Jern Cheng, Taipei (TW); Yu-Chih Lin, Taipei (TW); Han-Yen Tu, Taipei (TW)

(73) Assignee: National Taiwan Normal University, Taipei (TW)

( * ) Notice: Subject to any disclaimer, the term of this patent is extended or adjusted under 35 U.S.C. 154(b) by 0 days.

(21) Appl. No.: 15/628,272

(22) Filed: Jun. 20, 2017

(65) Prior Publication Data
US 2018/0266806 A1 Sep. 20, 2018

(30) Foreign Application Priority Data

Mar. 17, 2017 (TW) .............................. 106108982 A

(51) Int. Cl.
*A61B 5/00* (2006.01)
*G01B 9/02* (2006.01)
*G01B 9/04* (2006.01)
*G03H 1/00* (2006.01)
*G03H 1/04* (2006.01)
*G03H 1/08* (2006.01)
*G01B 9/021* (2006.01)

(52) U.S. Cl.
CPC ............ *G01B 9/021* (2013.01); *A61B 5/0066* (2013.01); *A61B 5/0073* (2013.01); *G01B 9/02038* (2013.01); *G01B 9/02041* (2013.01); *G01B 9/02047* (2013.01); *G01B 9/02083* (2013.01); *G01B 9/04* (2013.01); *G03H 1/0005* (2013.01); *G03H 1/0443* (2013.01); *G03H 1/0866* (2013.01)

(58) Field of Classification Search
CPC ...... G01B 9/021; G01B 9/02083; G01B 9/04; G03H 1/0866; G03H 1/0005; G03H 1/0443; A61B 5/0066; A61B 5/0073
See application file for complete search history.

(56) References Cited

U.S. PATENT DOCUMENTS

2015/0234350 A1* 8/2015 Park .................... G03H 1/2294
359/9

OTHER PUBLICATIONS

Su et al. "Digital holographic microtomography for high-resolution refractive index mapping of live cells", J. Biophotonics 6, No. 5, 416-424 (2013).*

(Continued)

*Primary Examiner* — Dominic J Bologna
(74) *Attorney, Agent, or Firm* — Muncy, Geissler, Olds & Lowe, P.C.

(57) ABSTRACT

A method for digital holographic microtomography comprises (a) providing at least one wavefront controlling device for driving a sample to be rotated and/or an incident beam scanning the sample, (b) utilizing a digital holographic access unit for recording the transmitted or reflected wavefronts of the sample, (c) utilizing a digital holography reconstructing method for reconstructing the transmitted or reflected wavefronts of the sample, and (d) utilizing a tomographic reconstruction approach for reconstructing three dimensional image information of the sample.

20 Claims, 10 Drawing Sheets

(56) References Cited

OTHER PUBLICATIONS

Chen Li-Ping and Lü Xiao-Xu, "The recording of digital hologram at short distance and reconstruction using convolution approach" 2009 Chinese Phys. B 18 189.*

Kyoji Matsushima and Tomoyoshi Shimobaba, "Band-Limited Angular Spectrum Method for Numerical Simulation of Free-Space Propagation in Far and Near Fields," Opt. Express 17, 19662-19673 (2009).*

Müller, Paul, Mirjam Schürmann, and Jochen Guck. "The theory of diffraction tomography." arXiv preprint arXiv:1507.00466 (2015).*

"Sectional imaging of spatially refractive index distribution using coaxial rotation digital holographic microtomography" Yu-Chih Lin and Chau-Jern Cheng 2014 J. Opt. 16 065401.*

* cited by examiner

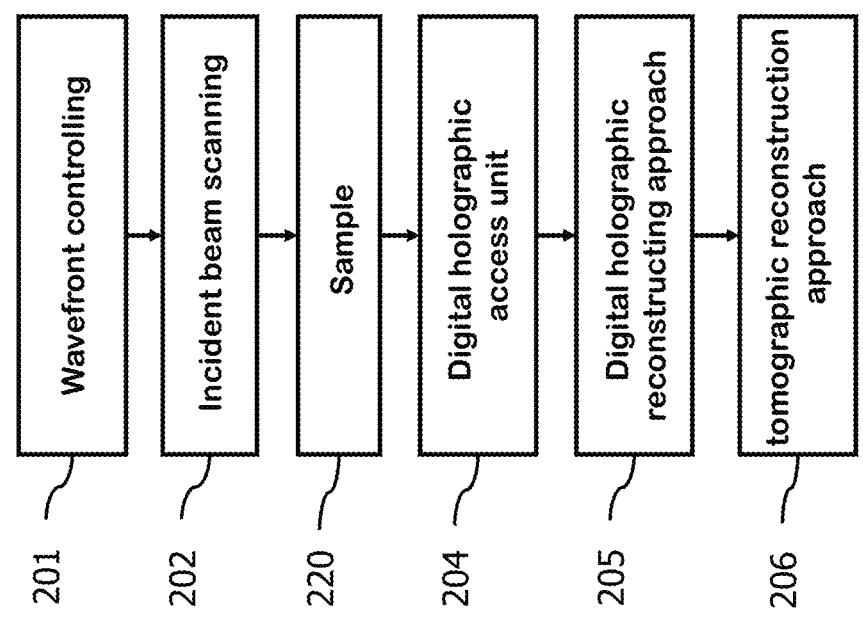
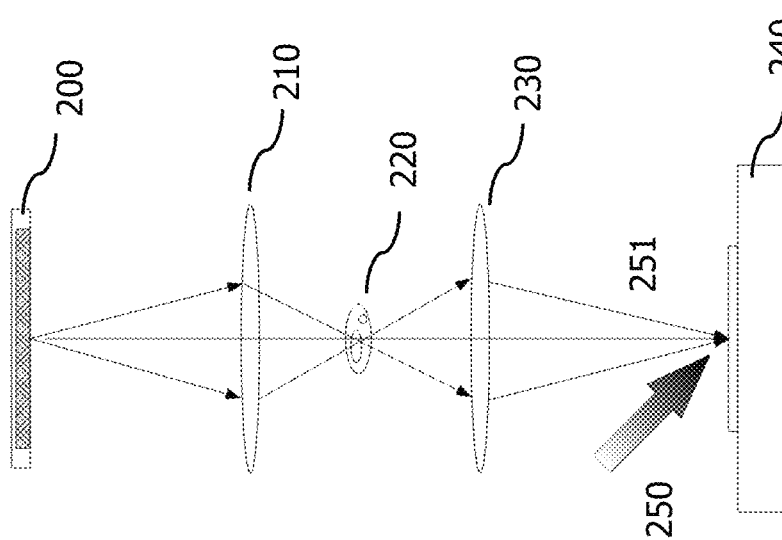
FIG.2

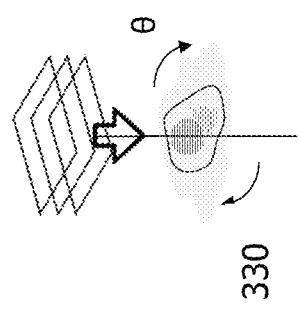
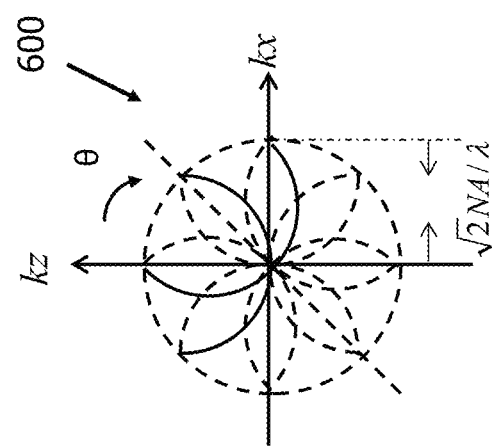
FIG.6

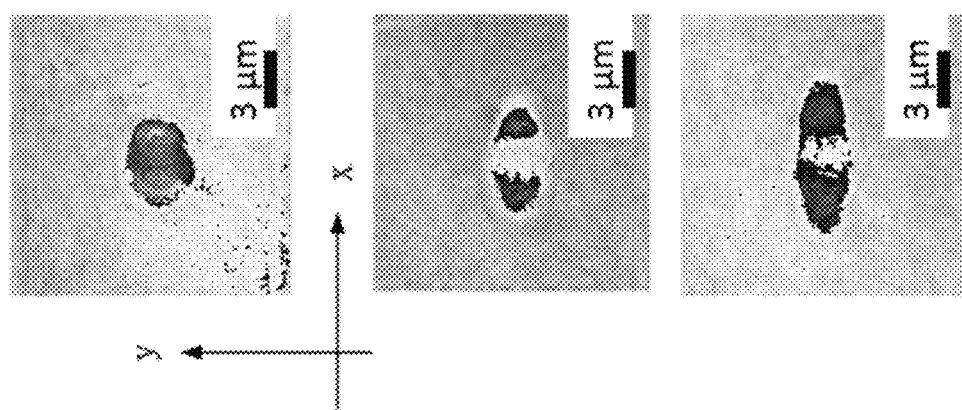

METHOD AND APPARATUS FOR DIGITAL HOLOGRAPHIC MICROTOMOGRAPHY

TECHNICAL FIELD

The present invention relates to an optical imaging technique, and more particularly, to a method and apparatus for digital holographic microtomography by an optically-driven for sample rotation and an incident beam scanning of the sample to achieve a high-resolution three-dimensional image.

BACKGROUND

Beam-rotation digital holographic microtomography utilizes the rotating mirror for changing incident angle of the incident beam onto a sample, and calculates the three-dimensional (3D) spectrum distribution of the measured sample by recording optical field of the incident beam at different angles, so as to achieve the three-dimensional refractive index distribution inside the sample. The method is applied to the observation of the images of living cells to reach the sub-micron lateral resolution. However, this method has poor longitudinal resolution, which will result in the difficulty of observing the complete 3D tomographic images.

Furthermore, measuring technology of the traditional holographic tomography further comprises:

(a) Sample-rotation digital holographic tomography: this technique is similar to the known computer tomography, which records transmitting optical field at different angle by surrounding the sample, and the general implementation is directly rotating the object to be tested or its carrier; can be applied for optical fiber detection, directly rotating optical fiber during digital holographic recording to reach the purpose of tomography information access; in addition can also be used for the detection of biomedical cell. The drawbacks include complex sample preparation and harsh shooting conditions, which results in disadvantage of biomedical system promotion. In addition, there are still some problems in the mechanical stability for the sample rotation mode improvement. A holographic optical tweezer is manipulated to directly rotating the sample, which three-dimensional resolution is affected by the restricted rotation angle.

(b) Optical coherence tomography: this technique is commonly used in the detection of biomedical living cells and tissues. It can be used to detect the samples of living organisms by optical slicing, based-on low coherence light source with short coherence window. It can be applied in clinic. The disadvantage is that it is difficult to apply to the detection of living cells due to the poor horizontal and vertical resolution.

(c) Fluorescence laser confocal microscope: this technology is commonly used in the detection of biomedical cells, through point-to-point, layer-by-layer scanning mechanism of confocal microscope, fluorescence dyeing and stimulated image information inside the sample are obtained. The disadvantage is that it has a low vertical resolution, and the dyeing has damaged the cells.

In recent years, Taiwan is actively developing life medicine and other related industries, and the output value is increased by 17% in the last year (2016). The government will invest billions of dollars to enter the relevant industries in order to reach the trillion output value in the future. The invention provides a tomographic imaging tool, which is expected to be used for the analysis of the structure of living cells and the diagnosis of biochemical characteristics. In addition, in the industrial inspection and fiber communication industry, the present invention can also be used in the detection of micro optical elements and particle structures, or for the detection of the internal structure and refractive index of optical fiber and the analysis of the optical waveguide characteristics. Due to long-term lack of innovation time-space detection mechanism in industrial inspection, the invention reveals its importance in the future development, and the terminal products can be expanded to the United States, being positive development of Photoelectric Industrial Technology. Therefore, it is very useful in industry, and has potential marketing.

However, at present, there is some drawbacks in holographic tomography technology for industrial applications. It is necessary to develop a novel tomography technology to solve the above problems.

SUMMARY OF THE INVENTION

In this invention, a method for digital holographic microtomography, comprising: (a) providing at least one wavefront controlling device for optically driving a sample to be rotated and/or an incident beam scanning said sample; (b) utilizing a digital holographic access unit for recording transmitting or reflecting wavefronts of said sample; (c) utilizing a digital holographic reconstruction approach for reconstructing said transmitting or reflecting wavefronts of said sample; and (d) utilizing a tomographic reconstruction approach for reconstructing three dimensional image information of said sample.

The at least one wavefront controlling device includes a spatial light modulator, an electrically controlled light reflector, a mirror loaded piezoelectric transducer or a liquid crystal on silicon device. The digital holographic access unit includes a photodetector array.

The digital holographic reconstruction approach includes Fourier transform approach, convolution approach, angular spectrum approach or Fresnel diffraction approximate approach.

The tomographic reconstruction approach includes back projection approach, back propagation approach, Fourier slice theorem approach or Fourier diffraction theorem approach.

An apparatus for digital holographic microtomography comprises at least one wavefront controlling device configured controlling wavefront of an incident beam for scanning a sample; at least one lens configured for collecting transmitting or reflecting wavefronts of the sample; and a photodetector array configured under the at least one lens.

An apparatus for digital holographic microtomography comprises at least one wavefront controlling device configured controlling wavefront of an incident beam for optically driving a sample to be rotated; at least one lens configured for focusing the incident beam and collecting transmitting or reflecting wavefronts of the sample; and a photodetector array configured under the at least one lens.

An apparatus for digital holographic microtomography comprises a first wavefront controlling device configured controlling wavefront of a first incident beam for scanning a sample; a second wavefront controlling device configured controlling wavefront of a second incident beam for optically driving the sample to be rotated; at least one lens configured for focusing the second incident beam and collecting transmitting or reflecting wavefronts of the sample; and a photodetector array configured under the at least one lens.

According to another aspect, the apparatus further comprises a beam splitting element configured in front of the second wavefront controlling device.

BRIEF DESCRIPTION OF THE DRAWINGS

The components, characteristics and advantages of the present invention may be understood by the detailed descriptions of the preferred embodiments outlined in the specification and the drawings attached:

FIG. 2 illustrates a simple scheme and processing procedures of forming the digital holographic microtomography according to one embodiment of the present invention;

FIG. 6 illustrates a bandwidth pattern of the sample rotation method according to an embodiment of the invention;

FIG. 10 illustrates the sectional images under an optically-driven sample rotation.

DETAILED DESCRIPTION

Figure 1:
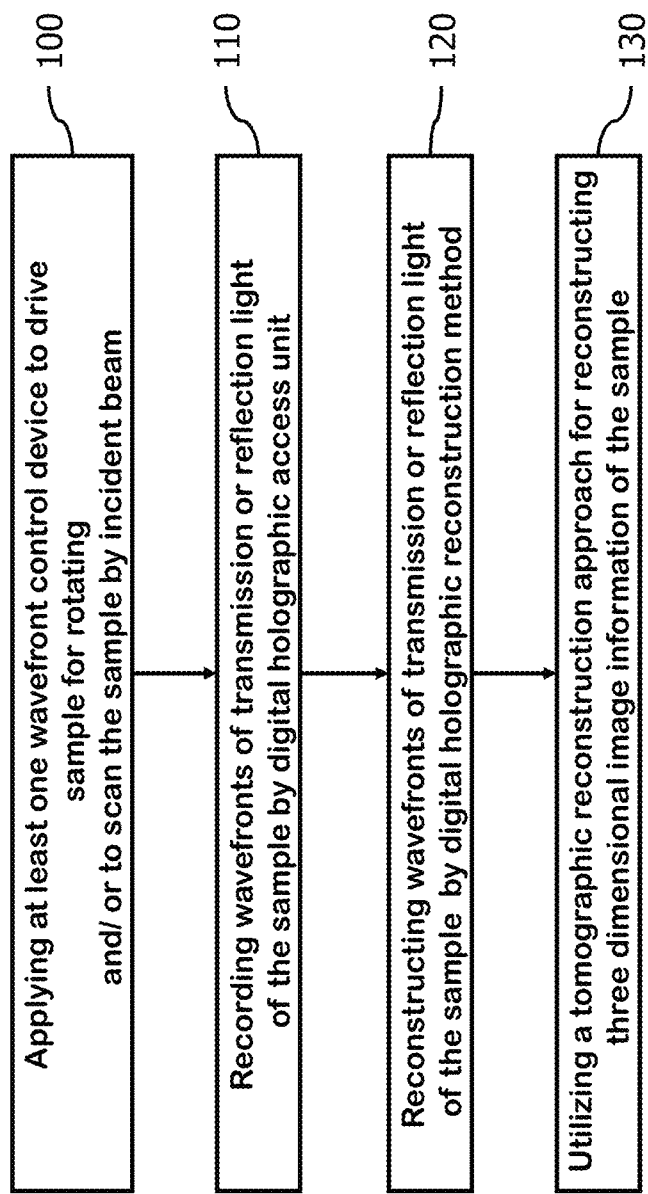
FIG. 1 illustrates the flow chart of forming the digital holographic microtomography according to the present invention.

Some preferred embodiments of the present invention will now be described in greater detail. However, it should be recognized that the preferred embodiments of the present invention are provided for illustration rather than limiting the present invention. In addition, the present invention can be practiced in a wide range of other embodiments besides those explicitly described, and the scope of the present invention is not expressly limited except as specified in the accompanying claims.

The invention presents a novel tomographic imaging technique for living biomedical samples using an optically-driven full-angle rotation scheme based on digital holographic microscopy, in which the three-dimensional reflective index distribution inside the sample can be measured and analyzed. The invention discloses a method and an apparatus for digital holographic microtomography, which utilizes the mechanism of beam scanning to improve the resolution of 3D tomography system, and further utilizes the beam (light) driving mechanism of sample rotation to accomplish the full-angle and full-direction scanning mechanism at the same time, and avoid information loss caused by angle restriction, and therefore reaches the same resolution in three-dimensional direction.

The invention can be applied to at least the following fields:

(a) Biomedical imaging: tomographic detection for internal of three-dimensional living cells free-of fluorescence and free-of dyeing, and analyzing three-dimensional spatial structure and biochemical characteristics of organelles through the refractive index characteristics of the organelles. Analysis of carcinogenesis: correctly analyzing Nuclear-to-Cytoplasmic ratio (NC ratio) through 3D tomographic detection of cancerous cells for realizing carcinogenesis in early phase.

(b) Semiconductor and industrial testing: detecting for micro optical components and micro particles refractive index, can be used to analyze the internal characteristics and defects of the components or substrate.

(c) Optical fiber communication: detecting for the refractive index distribution inside optical fiber, and result of the detection can be used to analyze the propagation characteristics of optical fiber coupling, fused biconical taper, and connection.

The invention discloses a method and an apparatus for digital holographic microtomography by digital holographic recording and reconstructing. An optically-driven process is applied so that the sample can be controlled for rotating up to full direction and full angle (360 degrees). The transmission/reflection optical field of the sample at different rotation angles can be provided for recording wavefront propagation information by a digital holographic access unit. In addition, using the beam scanning method, changing angle of incident beam of the digital holographic access unit to the sample, and using the digital holographic recording method, the transmission/reflection wavefront propagation information is then recorded at different incident angle to the sample. According to the digital holographic reconstruction, the transmission/reflection optical field of the sample under different rotation angles and the transmission/reflection optical field of the sample at different incident angles can be reconstructed. The reconstruction of the optical field at different rotation angle and incident angle can be calculated to obtain the three-dimensional tomographic information. Based on the full-angle optical field information and the high frequency diffraction information, the computed tomography images obtained by the proposed method can be used to obtain the ultra-high resolution imaging characteristics in three-dimensional space.

In order to meet the above-mentioned technical requirements, the invention provides a method and an apparatus for digital holographic microtomography. The apparatus of the invention includes: (1) at least one optical driven module: including a laser light source module, at least one spatial light modulator to control and drive optical field; (2) at least one beam scanning module: including at least one beam steering device (including electric rotary reflection mirror, grating, digital hologram); (3) at least one digital holographic access unit: including a laser light source module, including at least one image sensor to record wavefront information, and at least one computer (computing device, computer system).

As shown in FIG. 1, it illustrates the flow chart of forming the digital holographic microtomography according to the present invention. The present invention is applicable to the processing of at least one hologram image of a standard sample, for example including cells, microorganisms, bacteria, micro-size object, etc. The holographic images can be generated by optical systems of some embodiments. First, in the step 100, at least one wavefront control device is applied to drive the sample for rotating and/or to scan the sample by incident beam. The incident beam is provided by a laser light source module. The wavefront control device is included in at least one optical driven module and/or included in at least one beam scanning module. The optical driven module comprises at least one spatial light modulators (SLM). The beam scanning module comprises at least one beam steering device, which comprises an electrically controlled light reflector (for example, galvo mirror) and a grating. The wavefront control device includes but not limited to spatial light modulator, electrically controlled light reflector, mirror loaded piezoelectric transducer (PZT) to change the wavefront of an incident beam. The mirror loaded piezoelectric transducer can be used to adjust phase shift of the reference light, as phase shifter (e.g., PZT, spatial light modulator, phase shift element with rotated parallel plate). Next, in the step 110, the wavefronts of transmission or reflection light of the sample are recorded by the digital holographic access unit. The digital holographic access unit includes at least one photodetector arrays, such as an image sensor, for recording the wavefronts information, and a computing device used to digitally access the wavefronts information. In this step, the incident beam is used for sample detection, and the incident beam and the reference light is interfered with each other, and the interference information is recorded by at least one image sensor. Then, in the step 120, the wavefronts of transmission or reflection light of the sample is reconstructed by a digital holographic reconstruction method. The digital holographic reconstruction method includes but not limited to use numerical propagation approach of Fourier transform, convolution method, angular spectrum method or Fresnel diffraction approximate method to reconstruct the wavefront of transmission or reflection light of the sample. In the numerical reconstruction method of Fourier transform approach, the number of pixels will be changed with the reconstruction distance. This feature will make pixel size reduction of the reconstructed image, in order to avoid the actual pixel size of the photodetector array to be restricted, and at the same time to achieve the purpose of the image reconstruction. Finally, in the step 130, a tomographic reconstruction approach is used to reconstruct the 3D image information of the sample. The three-dimensional image information of the sample comprises the digital holographic microtomography of the sample. The tomographic reconstruction approach (image reconstruction method) includes but not limited to the method of back projection, back propagation, Fourier slice theorem, and Fourier diffraction theorem.

As shown in FIG. 2, it shows a simple scheme and processing procedures of forming the digital holographic microtomography according to one embodiment of the present invention. The embodiment of the present invention is utilizing an incident beam to scan the sample to produce a digital holographic microtomography. An optical system generates a detection beam and a reference beam. For example, the optical system includes a light source, at least one beam splitter, a wavefront control device, at least one photodetector array (for example: Charge-coupled device (CCD), Complementary Metal-Oxide-Semiconductor (CMOS) image sensor, photodetector), multiple lenses and multiple mirrors. The light source includes a vertical-cavity surface-emitting laser (VCSEL), a semiconductor laser, a solid-state laser, a gas laser, a dye laser, a fiber laser or light emitting diodes (LED). The emission type of the light source comprises a light source, a planar light source or a spherical light source. The light source includes coherent light source, low coherent light source or incoherent light source. The optical system includes an optical image resizing system, which includes a lens 210 and a lens 230, for collecting the wavefront of transmitted or reflected light of the sample. The optical path of the optical system includes: a diode laser emits a probe beam with a specific central wavelength, the probe beam reflecting by the mirrors and passing through a beam expander to generate an expanded beam, then incident into the beam splitter to output two beams respectively. One beam of the two beams is passing through the wavefront control device 200 to change wavefront of the incident beam, and therefore creating beam inflection. Then, the incident beam is passing through the lens for incident to the sample 220 by an incident angle. In one embodiment, the lens 210 may be incorporated into the wavefront control device 200. The incident beam is passing through the sample 220 or reflecting by the sample 220, and followed by collecting and magnifying by the lens 230 to form a magnified beam 251. The other beam of the two beams is reflected by the mirror as the reference wave 250. The magnified beam 251 is interfering with the reference wave 250. The interfered wave is then recorded by the photodetector array (image sensor) 240 to obtain a digital holographic recording.

Figure 5:
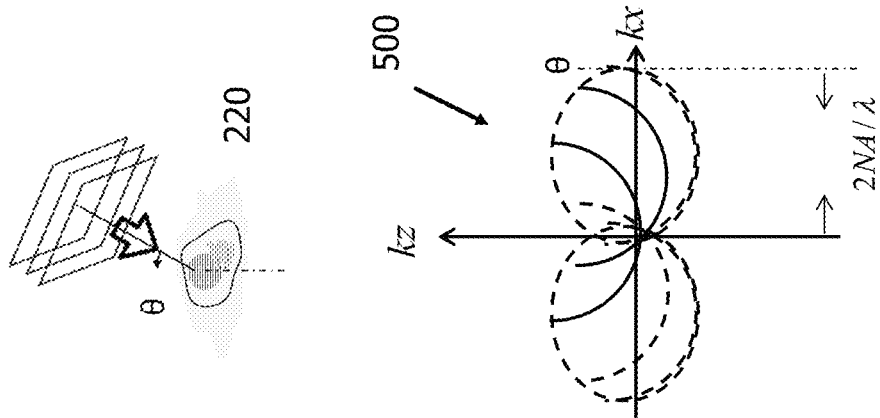
FIG. 5 illustrates a bandwidth pattern of the beam rotation method according to an embodiment of the invention.

The above-mentioned mirrors are only used to redirect the optical path of the laser beam. The above-mentioned lenses can be regarded as the element which can generate the beam expanding wavefront (plane wave and spherical wave), a planar, a spherical or an arbitrary surface wavefront. The wavefront control device 200 includes at least one spatial light modulators (SLM) or electrically controlled light reflector to change wavefront of the incident beam. The processing procedures of forming the digital holographic microtomography includes utilizing the wavefront control device 200 for wavefront controlling 201 of the incident beam. The wavefront of the incident beam is changed to cause beam deflection, and thereby forming an incident beam scanning 202, as shown in FIG. 5. In other words, in this embodiment, the incident beam scanning 202 is the result of performing a beam rotation process. The wavefront of the transmitted beam of the sample transformed by Fourier transformation may be forming bandwidth pattern 500 shown in FIG. 5. Therefore, the spectrum bandwidth in Fourier plane has double resolution by the beam rotation process. For the beam rotation method, the transformed frequencies at different angles can be mapped into the frequency distribution as the following equation:

$$u_{TA}(x') = \int e^{jux'} du \int \int \frac{o(x,z)}{\beta} e^{-j(\beta-k)z} e^{-j(u-k\theta)x} dxdz$$

Wherein $u_{TA}(x')$ is optical field of the transmitted or reflected beam by the beam rotation, $o(x,z)$ is spatial distribution of the measured sample, z is distance between the sample and the image sensor, k is wave number, $\theta$ is rotation angle of the beam, u is frequency spectrum coordinate of the reconstructed image, and $\beta$ is Ewald's sphere curvature parameter.

Then, the incident beam is passing through the sample 220 or reflecting from the sample 220. The interfered wave information of the magnified beam (wave) 251 and the reference wave 250 is processed by the digital holographic access unit 204 to obtain digital holographic recording. Subsequently, the digital holographic reconstructing approach 205 is utilized for reconstructing the transmitted or reflected beam wavefront of the sample 220. Finally, the tomographic reconstruction approach 206 is utilized for reconstructing three dimensional image information of the sample 220. The three dimensional image information of the sample includes the digital holographic microtomography of the sample 220. The digital holographic microtomography of the sample may be so called computed tomography (CT).

In some embodiments, the holograms may be utilized by mechanically moving photodetector array, the measured object and incident beam for expanding wide field to generate digital hologram of on-axis, off-axis, in-line or common-path optical scheme.

Figure 3:
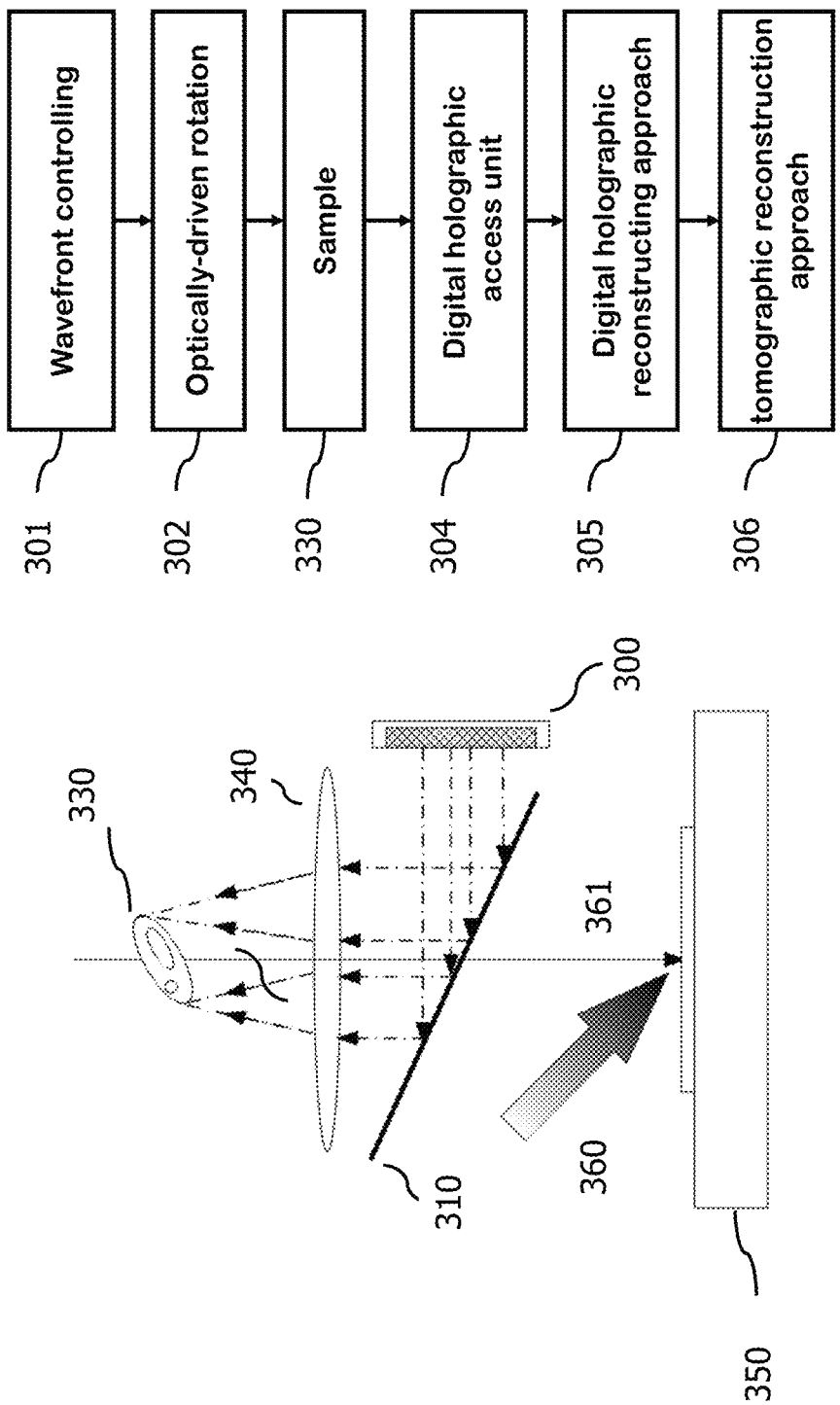
FIG. 3 illustrates a simple scheme and processing procedures of forming the digital holographic microtomography according to another embodiment of the invention.

As shown in FIG. 3, it shows a simple scheme and processing procedures of forming the digital holographic microtomography according to one another embodiment of the present invention. The embodiment of the present invention is utilizing an optically-driven sample rotation to produce a digital holographic microtomography. An optical system generates a detection beam and a reference beam. For example, the optical system includes a light source, at least one beam splitter, a wavefront control device, at least one photodetector array, multiple lenses and multiple mirrors. The optical system includes an optical image resizing system, which includes at least one lens (or lenses set) 340, for focusing the incident beam and collecting the wavefront of transmitted or reflected beam of the sample. The optical path of the optical system includes: a diode laser emits a probe beam with a specific central wavelength, the probe beam reflecting by the mirrors and passing through a beam expander to generate an expanded beam, controlled by the wavefront control device 300 and then incident into a beam splitting element 310 to output two beams respectively. The beam splitting element 310 is configured in front of the wavefront control device 300 and under the lens 340. One beam of the two beams is passing through the wavefront control device 300 to change wavefront of the incident beam, and encoding the wavefront distribution. Then, the incident beam is passing through the beam splitting element 310. In one embodiment, the beam splitting element 310 includes a beam splitter or a dichroic mirror. The dichroic mirror allows for a specified wavelength light reflected and other wavelengths light passing through. The encoded wavefront of the trap beam is propagating through the lens 340 to form at least one focusing point at different position and distance. The at least one focusing point is traced to control the sample 330 for its rotation. As the sample 330 is conducted by an angle of rotation, the optical field of the transmitted or reflected beam of the sample may be obtained by the incident beam of the digital holographic access unit. The optical field of the incident beam transmitting through the sample 330 or reflecting from the sample 330, is passing through the lens 340 to be collected and magnified for forming a magnified beam 361. The other beam of the two beams is reflected by the mirror as the reference wave 360. The transmitted or reflected magnified beam 361 is interfering with the reference wave 360. The interfered wave is then recorded by the photodetector array (image sensor) 350 to obtain a digital holographic recording.

As shown in FIG. 3, the wavefront control device 300 includes at least one spatial light modulators (SLM) or electrically controlled light reflector to change wavefront of the incident beam. The processing procedures of forming the digital holographic microtomography includes utilizing the wavefront control device 300 for wavefront controlling 301 of the incident beam. The controlled wavefront of the incident beam is forming a mechanism of optically-driven rotation 302 by the beam splitter 310 and the lens 320, as shown in FIG. 6. In other words, in this embodiment, the optically-driven rotation 302 is the result of performing a sample rotation process. The wavefront of the transmitted beam of the sample transformed by Fourier transformation may be obtaining bandwidth pattern 600 shown in FIG. 6. Therefore, the spectrum bandwidth in Fourier plane has double resolution by the beam rotation process. For the sample rotation method, the transformed frequencies at different angles can be mapped into the frequency distribution as the following equation:

$$u_{TR}(x') = \int e^{jux'} du \int \int \frac{o(x,z)}{\beta} e^{-j(\beta-k+u\theta)z} e^{-j(u-k\theta+\beta\theta)x} dx dz$$

Wherein $u_{TR}(x')$ is optical field of the transmitted or reflected beam by the sample rotation, $o(x,z)$ is spatial distribution of the measured sample, z is distance between the sample and the image sensor, k is wave number, $\theta$ is rotation angle of the sample, u is frequency spectrum coordinate of the reconstructed image, and $\beta$ is Ewald's sphere curvature parameter.

Then, the incident beam is passing through the sample 330 or reflecting from the sample 330. The interfered wave information of the magnified beam (wave) 361 and the reference wave 360 is processed by the digital holographic access unit 304 to obtain digital holographic recording. Subsequently, the digital holographic reconstructing approach 305 is utilized for reconstructing the transmitted or reflected beam wavefront of the sample 330. Finally, the tomographic reconstruction approach 306 is utilized for reconstructing three dimensional image information of the sample 330. The three dimensional image information of the sample includes the digital holographic microtomography of the sample 330.

Figure 4:
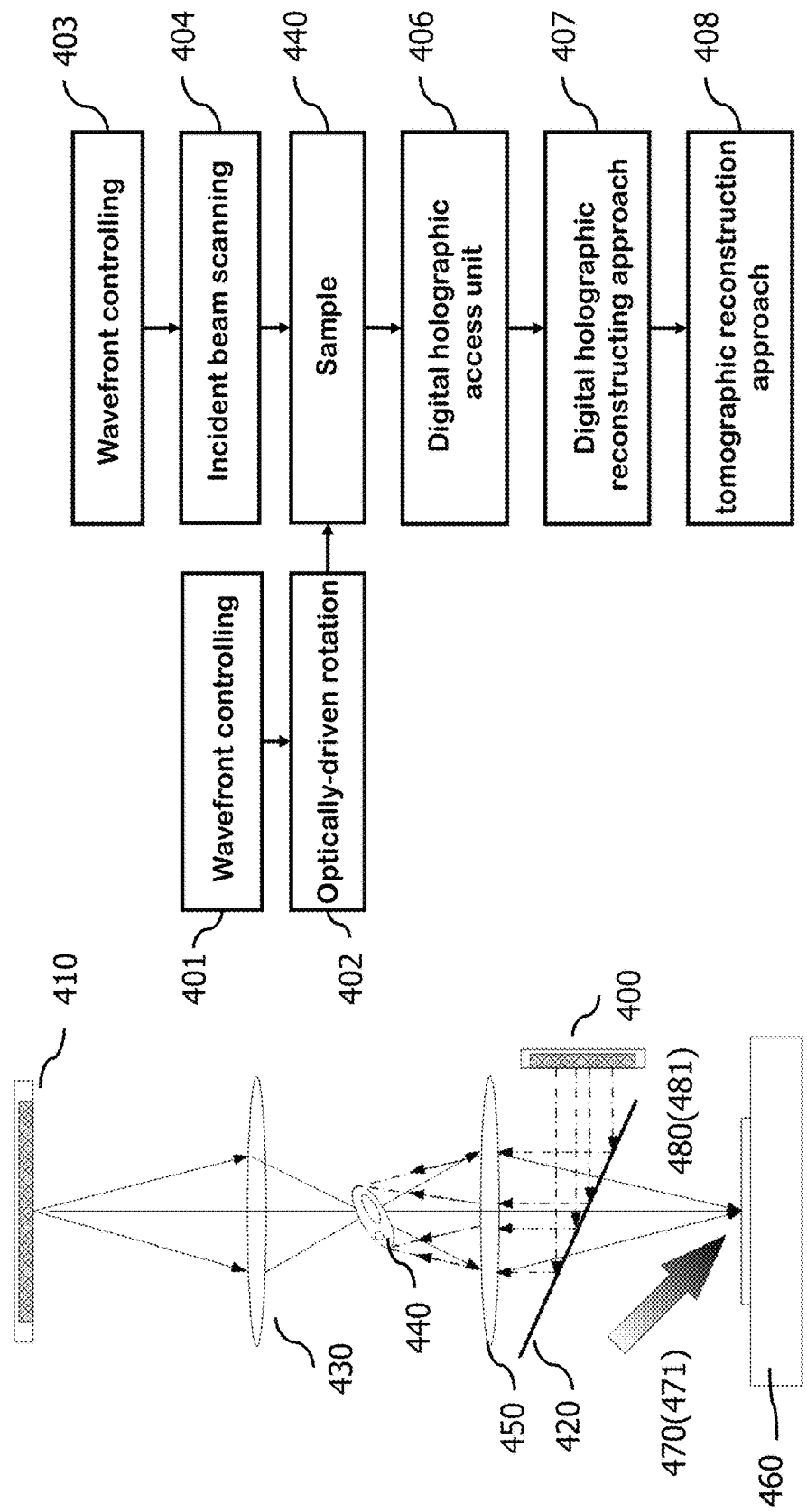
FIG. 4 illustrates a simple scheme and processing procedures of forming the digital holographic microtomography according to yet another embodiment of the invention.

As shown in FIG. 4, it shows a simple scheme and processing procedures of forming the digital holographic microtomography according to yet another embodiment of the present invention. The embodiment of the present invention is utilizing an incident beam scanning the sample and an optically-driven sample rotation to produce a digital holographic microtomography. An optical system generates a detection beam and a reference beam. For example, the optical system includes at least one light source, at least one beam splitter, at least one wavefront control device, at least one photodetector array, multiple lenses and multiple mirrors. Similarly, the optical system includes an optical image resizing system, which includes a lens (or lens set) 430 and a lens (or lens set) 450, for focusing the incident beam and collecting the wavefront of transmitted or reflected beam of the sample. The beam splitter 420 is configured in front of the wavefront control device 400 and under the lens 450. The optical path of the optical system includes: (1) a first laser emits a probe beam with a specific central wavelength, the probe beam reflecting by the mirrors and passing through a beam expander to generate an expanded beam, controlled by the wavefront control device 400 and then incident into the beam splitter 420 to output two beams respectively; (2) a second laser emits a probe beam with a specific central wavelength, the probe beam reflecting by the mirrors and passing through a beam expander to generate an expanded beam, then incident into the lens 430, the sample 440, and the lens 450, and further to the beam splitter 420 to output two beams respectively.

First optical path: One beam of the first laser source is passing through the wavefront control device 410 to change wavefront of the incident beam, and therefore creating beam inflection. Then, the incident beam is passing through the lens 430 for incident to the sample 440 by an incident angle. The incident beam is passing through the sample 440 or reflecting by the sample 440, followed by collecting and magnifying by the lens 450, and incident into the beam splitter 420 to form a magnified beam 480. The other beam of the first laser source is reflected by the mirror as the reference wave 470. The magnified beam 480 is interfering with the reference wave 470 to form a first interference information.

Second optical path: One beam of the second laser source emits an optically-driven beam with a specific central wavelength, passing through the wavefront control device 400 to change wavefront of the incident beam, and encoding the wavefront distribution. Then, the incident beam is passing through the beam splitter 420. The encoded wavefront of the trap beam (optically-driven beam) is propagating through the lens 450 to form at least one focusing point at different position and distance. The at least one focusing point is traced to control the sample 440 for its rotation. As the sample 440 is conducted by an angle of rotation, the optical field of the transmitted or reflected beam of the sample may be obtained by the incident beam of the digital holographic access unit. The optical field of the incident beam transmitting through the sample 440 or reflecting from the sample 440, is passing through the lens 450 to be collected and magnified for forming a magnified light wave 481. The other beam of the second laser source is reflected by the mirror as the reference wave 471. The transmitted or reflected magnified light wave 481 is interfering with the reference wave 471 to form a second interference information. The first interference information and the second interference information is then recorded by the photodetector array (image sensor) 460 to obtain a digital holographic recording.

In one embodiment, two light waves interference is forming at least one holographic image as wavefront recording of digital holographic image and the following wavefront reconstructing and tomographic reconstruction to obtain a digital holographic microtomography of the sample. the reference wave includes a planar wave, a spherical wave or an arbitrary surface wave. The digital holographic image of the sample includes amplitude image and phase image.

Figure 7:
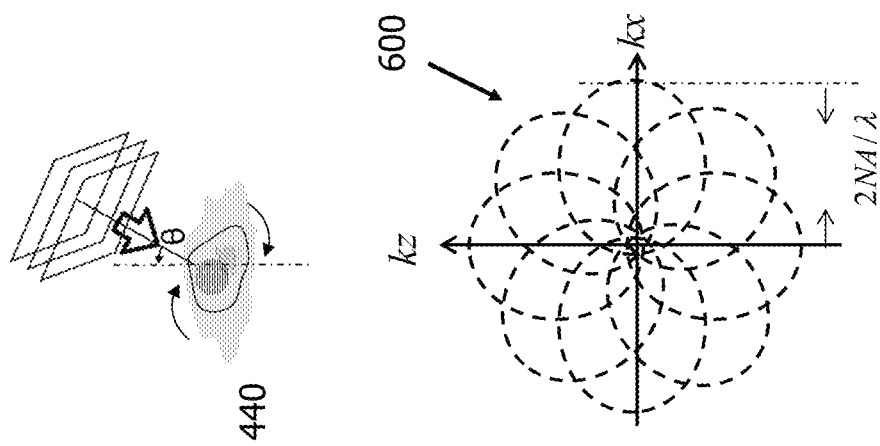
FIG. 7 illustrates a bandwidth pattern of the beam rotation method combined with the sample rotation method according to one embodiment of the invention.

As shown in FIG. 4, the wavefront control device 400, the wavefront control device 410 includes at least one spatial light modulators (SLM), electrically controlled light reflector, or liquid crystal on silicon (LCoS) device to change wavefront of the incident beam. In this embodiment, the processing procedures of forming the digital holographic microtomography includes: (a) utilizing the wavefront control device 410 for wavefront controlling 403 of the first incident beam, which wavefront is changed to cause beam deflection, and thereby forming an incident beam scanning 404; (b) simultaneously utilizing the wavefront control device 400 for wavefront controlling 401 of the second incident beam, which wavefront is forming a mechanism of optically-driven rotation 402 by the beam splitter 420 and the lens 450. Therefore, in this embodiment, the wavefront of the transmitted beam of the sample transformed by Fourier transformation may be obtaining bandwidth pattern 700 shown in FIG. 7, which is combined incident beam scanning sample method (shown in FIG. 5) with optically-driven sample rotation method (shown in FIG. 6).

Then, the incident beam is passing through the sample 440 or reflecting from the sample 440. The interfered wave information of the magnified wave 470 (471) and the reference wave 480 (481) is processed by the digital holographic access unit 406 to obtain digital holographic recording. Subsequently, the digital holographic reconstructing approach 407 is utilized for reconstructing the transmitted or reflected beam wavefronts of the sample 440. Finally, the tomographic reconstruction approach 408 is utilized for reconstructing three dimensional image information of the sample 440. The three dimensional image information of the sample includes the digital holographic microtomography of the sample 440.

Figure 8:
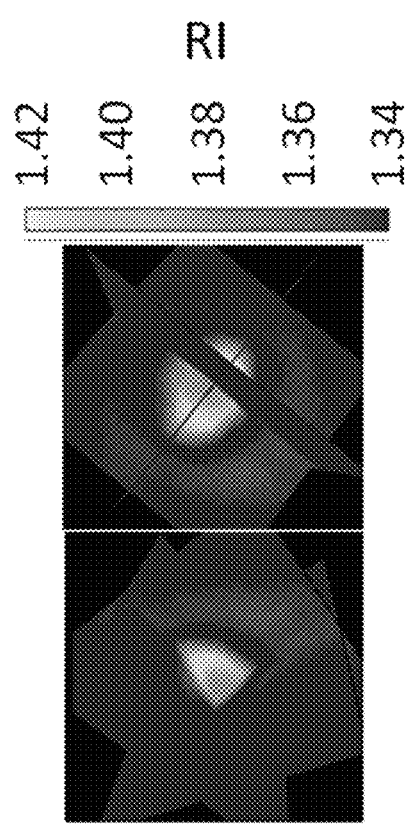
FIG. 8 illustrates the three-dimensional refractive index (3D RI) distribution of the living yeast.
Figure 9:
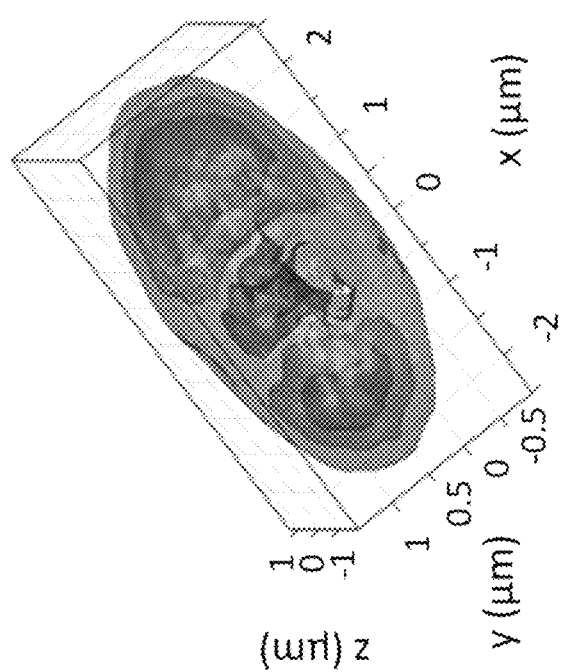
FIG. 9 illustrates the organelles inside the living yeast.

FIG. 8 shows the three-dimensional refractive index (3D RI) distribution of the living yeast. According to the above-mentioned three type of the digital holographic microtomography, the quantitative RI of the yeast in x-y-z space can be found and estimated as plotted in FIG. 8. By calculating the standard deviation of the RI of the surrounding medium, the measured accuracy of the refractive index in the 3D tomographic image can be reduced to approximately 0.006. In addition, the spatial resolution can be obtained by analyzing the boundary slope of the yeast edge in the reconstructed image, which shows that a spatial resolution of approximately 0.6 µm can be achieved in the x-, y-, and z-directions. To emphasize the contour features and the distribution of the yeast from the RI data, the organelles inside the living yeast can be readily obtained, as shown in FIG. 9. Therefore, the quantitative RIs of the nucleus and cytoplasm are defined approximately from 1.42 to 1.36 according to a comparison the RI data in FIG. 8 and the structure of the yeast in FIG. 9. The RI of the vacuole inside the yeast is therefore approximately 1.34. The contouring result is consistent with the true sizes of the organelles inside yeast.

To confirm that the missing apple core (MAC) problem can be refilled and compensated for by the full-angle rotation without the need for any additional iterative algorithms for data retrieval, the refractive index images (raw data) of the yeast are directly shown and compared in FIG. 10, which includes the sectional images under an optically-driven sample rotation along the x-z- and y-z-directions. For the x-z rotation only, the sectional images are shown in the upper of the FIG. 10; the image is blurred and unresolvable due to the MAC problem along the y-axis. For the full-angle rotation, images of the internal organelles still cannot be observed due to the defocusing effect on the rim of the sample during the rotation, as shown in the middle of the FIG. 10. The boundary of the yeast image is still blurred and unrecognizable due to the defocusing effect on the rim of the yeast during the holographic recording. After numerical focusing via the digital holographic microtomography (DHM) reconstruction, a clearer yeast image can be obtained, as shown in the lower of the FIG. 10, where some organelles (for example, the nucleus and vacuole) are observable in the reconstructed raw data of the tomographic image.

As mentioned previously, the invention discloses a mechanism of optically-driving sample rotation, for transmitted optical field scanning mechanism with full angle and full direction of the sample, and the mechanism of beam scanning to improve spatial resolution of 3D microtomography system of the present invention. The scanning optical field is recorded in the digital holograms by digital holographic wavefront recording approach for numerical reconstruction, and the reconstructed optical field correspondingly fills in 3D spectrum space of the tomographic images according to the scanning angle and the scanning method. The three dimensional (3D) spectrum can be used to calculate and analyze the 3D tomographic images.

The experimental results show that the digital holographic microtomography created by the digital holographic apparatus and method can achieve the purpose of 3D high-resolution imaging, beyond the existing optical tomography method.

As will be understood by persons skilled in the art, the foregoing preferred embodiment of the present invention illustrates the present invention rather than limiting the present invention. Having described the invention in connection with a preferred embodiment, modifications will be suggested to those skilled in the art. Thus, the invention is not to be limited to this embodiment, but rather the invention is intended to cover various modifications and similar arrangements included within the spirit and scope of the appended claims, the scope of which should be accorded the broadest interpretation, thereby encompassing all such modifications and similar structures. While the preferred embodiment of the invention has been illustrated and described, it will be appreciated that various changes can be made without departing from the spirit and scope of the invention.

What is claimed is:

1. A method for digital holographic microtomography, comprising:
   (a) utilizing a first wavefront controlling device to beam scan a sample at different incident angles and a second wavefront controlling device to optically drive said sample at different rotating angles to achieve full-direction and full-angle rotating of said sample;
   (b) utilizing a digital holographic access unit for recording transmitting or reflecting wavefronts of said sample at different incident angles and different rotating angles;
   (c) utilizing a digital holographic reconstruction approach for reconstructing said transmitting or reflecting wavefronts of said sample at different incident angles and different rotating angles; and
   (d) utilizing a tomographic reconstruction approach for reconstructing three dimensional image of said sample based on full-direction and full-angle rotating optical field information.

2. The method of claim 1, wherein said first or second wavefront controlling device includes a spatial light modulator.

3. The method of claim 1, wherein said first or second wavefront controlling device includes an electrically controlled light reflector.

4. The method of claim 1, wherein said first or second wavefront controlling device includes a mirror loaded piezoelectric transducer.

5. The method of claim 1, wherein said first or second wavefront controlling device includes a liquid crystal on silicon device.

6. The method of claim 1, wherein said digital holographic access unit includes a photodetector array or an image sensor.

7. The method of claim 1, wherein said digital holographic reconstruction approach includes Fourier transform approach.

8. The method of claim 1, wherein said digital holographic reconstruction approach includes convolution approach.

9. The method of claim 1, wherein said digital holographic reconstruction approach includes angular spectrum approach.

10. The method of claim 1, wherein said digital holographic reconstruction approach includes Fresnel diffraction approximate approach.

11. The method of claim 1, wherein said tomographic reconstruction approach includes back projection approach.

12. The method of claim 1, wherein said tomographic reconstruction approach includes back propagation approach.

13. The method of claim 1, wherein said tomographic reconstruction approach includes Fourier slice theorem approach.

14. The method of claim 1, wherein said tomographic reconstruction approach includes Fourier diffraction theorem approach.

15. An apparatus for digital holographic microtomography, comprising:
    a first wavefront controlling device to beam scan a sample at different incident angles;
    a second wavefront controlling device to optically drive said sample at different rotating angles, utilizing said first wavefront controlling device and said second wavefront controlling device to achieve full-direction and full-angle rotating of said sample;
    at least one lens configured to collect transmitting or reflecting wavefronts of said sample at different incident angles and different rotating angles; and
    a photodetector array or an image sensor configured under said at least one lens.

16. The apparatus of claim 15, wherein said first or second wavefront controlling device includes a spatial light modulator.

17. The apparatus of claim 15, wherein said first or second wavefront controlling device includes an electrically controlled light reflector.

18. The apparatus of claim 15, wherein said first or second wavefront controlling device includes a mirror loaded piezoelectric transducer.

19. The apparatus of claim 15, wherein said first or second wavefront controlling device includes a liquid crystal on silicon device.

20. The apparatus of claim 15, further comprising a beam splitting element configured in front of said second wavefront controlling device.

* * * * *